(12) United States Patent
Novikov et al.

(10) Patent No.: US 8,586,017 B2
(45) Date of Patent: Nov. 19, 2013

(54) SELF-HEATING NON-AEROSOL SHAVE PRODUCT

(75) Inventors: Alexander Novikov, Framingham, MA (US); Honorio V. Obias, Medford, MA (US); Yun Xu, Andover, MA (US); Alfred G. Barnet, Hingham, MA (US); Stephen H. Thong, Pennington, NJ (US)

(73) Assignee: The Gillette Company, Boston, MA (US)

( * ) Notice: Subject to any disclaimer, the term of this patent is extended or adjusted under 35 U.S.C. 154(b) by 1966 days.

(21) Appl. No.: 10/914,428

(22) Filed: Aug. 9, 2004

(65) Prior Publication Data

US 2006/0029566 A1 Feb. 9, 2006

(51) Int. Cl.
*A61Q 9/02* (2006.01)
*A61K 8/22* (2006.01)
*A61K 8/23* (2006.01)
*A61K 8/19* (2006.01)
*A61K 8/02* (2006.01)
*B65D 35/22* (2006.01)

(52) U.S. Cl.
USPC ............. 424/73; 424/401; 424/70.31; 222/94

(58) Field of Classification Search
USPC ............................. 424/73, 401, 70.31; 222/94
See application file for complete search history.

(56) References Cited

U.S. PATENT DOCUMENTS

| | | | |
|---|---|---|---|
| 2,995,521 A | 8/1961 | Bluard | |
| 3,341,418 A | 9/1967 | Moses et al. | |
| 3,454,198 A | 7/1969 | Flynn | |
| 3,484,378 A | 12/1969 | Reich et al. | |
| 3,488,287 A | 1/1970 | Seglin et al. | |
| 3,499,844 A | 3/1970 | Kibbel, Jr. et al. | |
| 3,574,118 A | 4/1971 | Baker | |
| 3,585,982 A | 6/1971 | Hollinshead | |
| 3,632,516 A * | 1/1972 | Antonelli et al. ............. 510/372 |
| 3,638,786 A | 2/1972 | Borecki et al. | |
| 3,639,574 A | 2/1972 | Schmolka | |
| 3,651,931 A | 3/1972 | Hsiung | |
| 3,722,752 A | 3/1973 | Kenkare et al. | |
| 3,723,324 A | 3/1973 | Pierce et al. | |
| 3,772,203 A | 11/1973 | Gray | |
| 3,819,524 A | 6/1974 | Schubert et al. | |
| 3,865,930 A | 2/1975 | Abegg et al. | |
| 3,866,800 A | 2/1975 | Schmitt | |
| 3,878,118 A | 4/1975 | Watson | |
| 3,931,912 A | 1/1976 | Hsiung | |
| 3,966,090 A | 6/1976 | Prussin et al. | |
| 4,010,872 A | 3/1977 | Lozano et al. | |
| 4,042,520 A | 8/1977 | Frump et al. | |
| 4,046,874 A * | 9/1977 | Gabby et al. .................... 424/73 |
| 4,088,751 A | 5/1978 | Kenkare et al. | |
| 4,110,426 A | 8/1978 | Barnhurst et al. | |
| 4,130,501 A | 12/1978 | Lutz et al. | |
| 4,439,416 A | 3/1984 | Cordon et al. | |
| 4,687,663 A | 8/1987 | Schaeffer | |
| 4,839,081 A | 6/1989 | Church et al. | |
| 4,855,075 A * | 8/1989 | Casciani ....................... 510/506 |
| 4,892,729 A | 1/1990 | Cavazza | |
| 5,279,819 A * | 1/1994 | Hayes ............................ 424/73 |
| 5,538,720 A | 7/1996 | Jendryssek-Pfaff et al. | |
| 6,794,349 B2 * | 9/2004 | Hafkamp et al. ............. 510/356 |
| 6,916,468 B2 | 7/2005 | Lasota | |
| 2004/0166086 A1 | 8/2004 | Manivannan et al. ........... 424/73 |

FOREIGN PATENT DOCUMENTS

| | | |
|---|---|---|
| BE | 747 809 | 8/1970 |
| EP | 1 175 895 A2 | 1/2002 |
| FR | 2.060.247 | 9/1969 |
| GB | 1110557 | 4/1968 |
| GB | 1317771 | 5/1973 |
| JP | 2001323258 A | 11/2001 |
| WO | WO 02/47636 A2 | 6/2002 |

OTHER PUBLICATIONS

Nonionic Surfactants in the Industrial Triad (Technical Insights). Frost & Sullivan Research Service. Published: Feb. 2, 2002. Accessed Apr. 11, 2008 <http://www.frost.com/prod/servlet/report-brochure.pag?id=D480-01-00-00-00>.*
PCT Search Report and Written Opinion in PCT/US2005/026829 (counterpart to U.S. Appl. No. 10/914,428).
Herbert Boden, "Hot Shave Lather Technology," "Freon" Products Laboratory, E.I. du Pont Nemours & Company (1968).
Solvay Interox, "Solvay Interox Formulary Guide Gelled Hydrogen Peroxide," Peroxygens, Techniccal Data Sheet (Apr. 1994).
Office Actions rejections/objections from co-pending U.S. Appl. No. 10/720,531, 14 pages.
Office Actions rejections/objections from co-pending U.S. Appl. No. 10/914,427, 36 pages.

* cited by examiner

*Primary Examiner* — Rachael E Bredefeld
(74) *Attorney, Agent, or Firm* — Joanne N. Pappas; Kevin C. Johnson; Steven W. Miller

(57) ABSTRACT

Self-heating non-aerosol shave products are provided. In some implementations, the shave product includes a non-ionic emulsifier system, for example, including one or more fatty alcohol ethoxylates.

30 Claims, No Drawings

SELF-HEATING NON-AEROSOL SHAVE PRODUCT

TECHNICAL FIELD

This invention relates to self-heating non-aerosol shave cream products.

BACKGROUND

Currently, a well-known form of shaving preparation is the type referred to as a non-aerosol shave gel. Such compositions generally take the form of an oil-in-water emulsion in which the water phase comprises a water-dispersible soap or interrupted soap component. The product is dispensed as a soft cream which may be non-lathering or which may be sheared by the user to form a lather.

Users of wet-shave razors generally appreciate a feeling of warmth against their skin during shaving. The warmth feels good, and also causes the user's skin to hydrate and beard to soften, resulting in a more comfortable shave. Various attempts have been made to provide a warm feeling during shaving. For example, soap-based shaving creams have been formulated to react exothermically upon release from the shaving canister, so that the cream imparts warmth to the skin, for example, as described in U.S. Pat. No. 3,341,418; U.S. Pat. No. 3,772,203; U.S. Pat. No. 3,819,524; U.S. Pat. No. 3,866,800; and U.S. Pat. No. 3,878,118.

SUMMARY

The invention features a self-heating non-aerosol shave cream product including a container with two separate chambers, one of which contains an oxidant component, and the other of which contains a reductant component. The container also has at least one opening for dispensing the contents of the chambers. The oxidant component includes a first shave cream base and an oxidizing agent, and the reductant component includes a second shave cream base and a reducing agent. The shave cream bases each independently include an oil-in-water emulsion including water and a water-dispersible surface active agent comprising a non-ionic surfactant. Preferably, one or both shave cream bases includes a thickener, which helps to stabilize viscosity. The amount and proportion of the oxidizing agent and the reducing agent are selected to provide an exothermic reaction with a desirable heat profile upon mixing of the oxidant component and the reductant component during use of the non-aerosol shave product. Because it is a non-aerosol product, it does not include any propellant or volatile foaming agent.

Preferably, at least one, or more preferably both, of the shave cream bases, are substantially free of soap and ionic surfactant (e.g., anionic surfactant). By "substantially free" is meant that the shave cream base contains less than about 2% of soap and ionic surfactant, preferably less than about 1.5% of soap and ionic surfactant, more preferably less than about 1% of soap and ionic surfactant, and most preferably 0% of soap and ionic surfactant.

The non-ionic, substantially soap-free formulation is compatible with, and stable in the presence of, the active agents that are used to generate the warm sensation. The non-ionic shave cream base may also offer additional advantages such as alleviating the problems associated with soap-based products. The non-ionic surfactant can include a blend of two surfactants, one of the surfactants being more hydrophobic than the other. Typically, the surfactant blend may include fatty alcohol ethoxylates having relatively longer and shorter polyethylene oxide chains (polyoxyethylene chains). For example, the blend may include a fatty alcohol ethoxylate having from 2 to 20 ethoxy groups, and a fatty alcohol ethoxylate having from 21 to 100 ethoxy groups, provided in a ratio in the range of from about 2.5:1 to about 1:2.5.

Preferably, the first shave cream base and the second shave cream base are substantially identical, by which is meant that each shave cream base has at least three, preferably at least four, ingredients identical to those in the other shave cream base and, most preferably, such ingredients are present in approximately the same proportions as in the other shave cream base.

Some implementations can exhibit one or more of the following advantages. The shave products provide a pleasant, warm feeling to the user before and during shaving, in combination with the aesthetic properties of a shave cream. The heating effect of the shave products helps to accelerate the hydration of a user's hair (e.g., beard) and prepare the hair for shaving, improving user comfort. The shave products dispense from their packaging in an attractive, aesthetic form. After being applied to a user's skin (e.g., to the user's face), the shave product remains on the skin during shaving (e.g., the cream does not run off of the face), even when the shave product is heated by the exothermic reaction. The shave product helps to soften hair (e.g., beard hair) and protects the skin during shaving. The shave product remains creamy and stable when the shave product is heated. The shave products provide desirable performance properties such as lubricity and skin-friendliness, which are maintained during and after heating. The chemistry of the heating system that is used to heat the shave products is safe for use on the skin and does not irritate the skin. After shaving, the shave product can be relatively easily removed from the skin.

Other features and advantages of the invention will be apparent from the description and from the claims.

DETAILED DESCRIPTION

As used in this application (unless indicated otherwise), all percentages are by weight on a solids basis.

The shave cream composition is divided into two separate components, (a) an oxidant component containing a first shave cream base and the oxidizing agent, and (b) a reductant component containing a second shave cream base and the reducing agent. Any ingredients that could be easily oxidized by the oxidizing agent during the product shelf life are included in the reductant component. These two components are maintained separate in the packaging of the shave cream composition, as will be discussed further below, and are mixed during or after dispensing. When the two components are mixed, an exothermic reaction occurs that heats the shave cream composition. If the exothermic reaction generates an acid that might tend to irritate the user's skin, then one component (preferably the reductant component) generally includes a neutralizing agent to neutralize this acid.

A preferred shave cream base for use in the present invention includes water and a water-dispersible surface active agent which comprises a non-ionic surfactant. Preferably, the water-dispersible surface active agent consists essentially of a non-ionic surfactant. Preferably, the non-ionic surfactant includes a blend of non-ionic surfactants, more preferably a blend of a relatively hydrophobic non-ionic surfactant and a relatively hydrophilic non-ionic surfactant. A more preferred shave cream base includes, in addition to the aforementioned ingredients, one or more (or, in a most preferred embodiment, all) of the following optional ingredients: a fatty alcohol, an emollient (e.g., an oil), and a thickener. The shave cream base is typically in the form of an oil-in-water emulsion.

The water-dispersible surface active agent, which is preferably a blend of surfactants, is selected to provide several functions. It functions as an emulsifier, solubilizer, detergent, and spreading or dispersing agent. First, the surfactants provide an emulsion that is stable during the shelf life of the product, allowing the product to be dispensed as a shave cream composition exhibiting little or no phase separation. Second, the surfactants provide lathering during creaming. Third, the surfactants are capable of providing a lather that will remain stable at elevated temperatures, i.e., the temperatures the shave cream composition can reach during heating, typically about from about 35° C. to about 50° C. By "stable," it is meant that the shave cream will not puddle in the user's hand or drip from the user's face, but will instead maintain substantially the same consistency before, during and after heating. The blend of surfactants is preferably present in both the oxidant and reductant components, so that both components can be provided as stable emulsions that can be dispensed in cream form.

The water-dispersible surface active agent includes a non-ionic surfactant, more preferably a blend of two or more non-ionic surfactants. Because they are stable in the presence of mild acids and alkalis, non-ionic surfactants can provide flexibility of formulation that is generally not possible using soaps. Preferred non-ionic surfactants include polyethoxylated fatty alcohol ethers. These are derived from fatty alcohols with C12-C24, preferably C12-C20, hydrocarbon chains (with a degree of unsaturation of 0-2) ethoxylated with about 2 to 150, preferably 2 to 100, ethylene oxide units (i.e., ethoxy groups). Thus, one or more of the fatty alcohol ethoxylates can have the general formula:

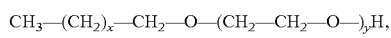

where x=10-22 (preferably 10-18), y=2-150 (preferably 2-100). Examples of such surfactants include Steareth-21, Steareth-100, Myreth-4, Myreth-10, Laureth-4, and Laureth-35. In some embodiments, the water-dispersible surface active agent can include a mixture of non-ionic surfactants having long (C16-C24) hydrocarbon chains and/or non-ionic surfactants having medium (C12-C14) hydrocarbon chains.

The blend of fatty alcohol ethoxylates can include:
(a) at least one fatty alcohol ethoxylate with a long polyethylene oxide chain length (i.e., 21-150, preferably 21-100, ethylene oxide units or ethoxy groups) and at least one fatty alcohol ethoxylate with a short polyethylene oxide chain length (i.e., 2-20 ethylene oxide units or ethoxy groups); and/or
(b) at least one fatty alcohol ethoxylate with a long polyethylene oxide chain length and a different fatty alcohol ethoxylate with a long polyethylene oxide chain length; and/or
(c) at least one fatty alcohol ethoxylate with a short polyethylene oxide chain length and a different fatty alcohol ethoxylate with a short polyethylene oxide chain length.

Preferred long polyethylene oxide chain length fatty alcohol ethoxylates include Steareth-100 (100 indicates the polyethylene oxide chain length) and Steareth-21. Other long polyethylene oxide chain length fatty alcohol ethoxylates can be used, such as Ceteth-100, Oleth-100, Myreth-100, and Beheneth-100. These long polyethylene oxide chain length fatty alcohol ethoxylate surfactants have a preferred HLB range from 15 to 18. Suitable shorter polyethylene oxide chain length fatty alcohol ethoxylates include, for example, Steareth-2, Steareth-10, Ceteth-10, Ceteth-20, Steareth-20, Myreth-20, Oleth-20 and Beheneth-20. These shorter polyethylene oxide chain length fatty alcohol ethoxylate surfactants have a preferred HLB range from 4 to 16.

The short and long polyethylene oxide chain length surfactants are included in a ratio that provides the desired aesthetic and performance properties to the cream. Surfactant levels and types may be selected based on HLB matching of the ingredients (minus surfactants) with the HLB of the surfactant system. It is preferred to use a blend of high and low HLB surfactants to accomplish this. For example Steareth-2 (HLB 4.9) and Stereath-100 (HLB 18.8) can be blended to give an HLB of about 15. The surfactant level may be further optimized to provide desired stability and formulation aesthetics. Thus, the relative amounts of the two surfactants may be adjusted to obtain a desired balance of properties. For a shave cream with good consistency and lathering, a suitable ratio of the short polyethylene oxide chain (more hydrophobic) surfactant to the long polyethylene oxide chain (more hydrophilic) surfactant would generally be in the range of about 2.5:1 to about 1:2.5, respectively.

In addition to or as an alternative to ethoxylated surfactants, suitable surfactant blends can include one or more non-ethoxylated surfactants, such as fatty ether or ester surfactants (e.g., polyglyceryl fatty esters, sugar ethers, sugar esters, esters of sugar derivatives). Examples of polyglyceryl fatty esters include decaglyceryl dipalmitate, decaglyceryl oleate, decagylceryl stearate, hexaglyceryl monostearate/oleate, decaglyceryl myristate, hexaglyceryl myristate, decagylceryl laurate, hexaglyceryl laurate, and triglyceryl stearate. Examples of sugar ethers include cetearyl polyglucoside, behenyl polyglucoside, myristyl polyglucoside, and cocoyl polyglucoside. Examples of sugar esters include sucrose esters, such as sucrose monostearate and sucrose distearate. Examples of esters of sugar derivatives include sorbitan esters, such as sorbitan monostearate, sorbitan palmitate, sorbitan oleate, sorbitan sesquioleate, and sorbitan isostearate. Generally, such non-ethoxylated surfactants will be included in the reductant component unless they are also determined to be stable in the presence of oxidizing agent.

The total amount of the water-dispersible surface active agent in either or each shave cream base (or in the composition as a whole) is generally in the range of from about 2% to about 15%, preferably from about 3% to about 12%. Including too high a level of the surfactants may result in inefficient mixing of the shave cream bases, which can limit the exothermic reaction between the shave cream bases, thereby reducing the warmth of the shave cream. Including too low a level of the surfactants may result in instability of the shave cream composition. The blends of short and long chain length fatty alcohol ethoxylates discussed above can stabilize the oil droplets, which are distributed in the water phase and in which the blowing gas (creaming agent) resides.

In certain embodiments, the oxidant component of a shave cream composition may include from about 2% to about 8%, preferably from about 2% to about 6% of a non-ionic surfactant. In certain embodiments, the oxidant component may include from about 1% to about 6%, preferably from about 2% to about 4%, of a shorter polyethylene oxide chain length non-ionic surfactant, such as Steareth-2. Alternatively or additionally, the oxidant component may include from about 1% to about 6%, preferably from about 2% to about 4% of a long polyethylene oxide chain length non-ionic surfactant, such as Steareth-21. In some embodiments, the oxidant component may include from about 1% to about 6% of one non-ionic surfactant, and from about 1% to about 6% of another, different, non-ionic surfactant.

In certain embodiments, the reductant component of a shave cream composition may include from about 2% to about 12%, preferably from about 3% to about 8% of a non-ionic surfactant, such as Steareth-100 or Steareth-21. The reductant component may include more than one type of non-ionic surfactant. For example, the reductant component may include from about 1% to about 8% of one non-ionic surfactant (e.g., Steareth-21), and from about 1% to about 8% of another, different, non-ionic surfactant (e.g., Steareth-100).

Water is the major component of the composition and is used in sufficient quantities to solubilize or disperse the surfactant components and form the continuous phase of the oil-in-water emulsion, while providing a stable cream of suitable viscosity with desirable lathering and rinsing properties. It is added in a sufficient quantity (q.s) to bring the total of all components to 100%. The composition (i.e., each of the oxidant and reductant components independently) typically includes from about 55% to about 95%, preferably from about 60% to about 90%, more preferably about 65% to about 85%, water. In certain embodiments, the oxidant component of the shave cream composition can include about 60% to about 90%, preferably about 70% to about 85%, water. In some embodiments, the reductant component can include from about 55% to about 90%, preferably from about 70% to about 85%, water. In certain embodiments (e.g., embodiments in which the reductant component includes a triethanolamine neutralizer), the reductant component may include from about 58% to about 70% water.

It is preferred that one or both shave cream bases include an emollient, to provide desirable cosmetic properties. The oil phase of the emulsion can include any desired emollient that is safe for use in a shave cream composition, is compatible with the other ingredients of the composition, and provides the desired aesthetics and in-shave lubricity. Suitable emollients include mineral oil, petrolatum, squalane/squalene, hydrogenated/unsaturated polyisobutene and mixtures thereof. These emollients are suitable for use with the surfactant blends discussed above. Preferably, the composition contains from about 0.25% to about 15% of the emollient, more preferably from about 0.5% to about 12% of the emollient, and most preferably from about 0.75% to about 8% of the emollient. The emollient is preferably included in both shave cream bases. In some embodiments, the oxidant component of a shave cream composition can include from about 1% to about 4% of an emollient (e.g., mineral oil). In certain embodiments, the reductant component of a shave cream composition can include from about 1% to about 5% of an emollient (e.g., mineral oil).

A thickener is optionally included to improve the consistency and stability of the shave cream, as well as to adjust its viscosity. The thickener also generally provides body to the shave cream. The thickener may be a water-soluble thickener, a water-insoluble thickener, or a mixture thereof. In some embodiments, either or both (preferably both) components of a shave cream composition can include from about 0.01% to about 15%, preferably about 0.1% to about 11%, of a thickener. In certain embodiments, the oxidant component and/or the reductant component of a shave cream composition can each include from about 1% to about 10%, preferably from about 3% to about 6% of a thickener. The thickener included in the oxidant component must, of course, be stable in the presence of an oxidizing agent (such a thickener includes, for example, polyvinylpyrrolidone).

A preferred thickener is a fatty alcohol (which is a water-insoluble thickener). Suitable fatty alcohols have a chain length of 12-22 carbon atoms, and a degree of unsaturation of 0-1. Suitable fatty alcohols include, for example, myristyl alcohol, lauryl alcohol, cocoyl alcohol, cetyl alcohol, cetearyl alcohol, oleyl alcohol, stearyl alcohol and behenyl alcohol. Generally the composition can include from about 0% to about 15%, preferably about 0.1% to about 15%, more preferably about 1% to about 15%, most preferably about 2% to about 8%, of a fatty alcohol thickener.

Other examples of suitable water-insoluble thickeners include ethoxylated fatty esters (e.g., PEG-150 distearate, PEG-150 pentaerythrityl tetrastearate), fatty esters (e.g., pentaerythrityl tetraisostearate, pentaerythrityl tetrastearate, isostearyl neopentanoate, and mixtures thereof) and high melting point waxes (e.g., hydrogenated castor oil). Such thickeners are particularly desirable to maintain product viscosity at the temperatures reached during the exothermic reaction and prevent it from running off the user's skin. In some embodiments, the oxidant component and/or the reductant component of a shave cream composition can include from about 0.1% to about 3% of such a thickener, such as hydrogenated castor oil or PEG-150 distearate.

In addition to, or in some cases instead of, the fatty alcohol thickener, the composition may include other thickeners. Examples of other suitable thickeners include water-soluble thickeners, such as hydroxyalkyl cellulose polymers, e.g., hydroxyethyl cellulose and hydroxypropyl cellulose (sold under the trademarks NATROSOL and KLUCEL respectively), carboxymethyl cellulose, cellulose methyl ether (sold under the trademark METHOCEL), hydroxypropyl starch phosphate (sold under the trademark STRUCTURE XL), other polysaccharides such as xanthan gum, guar gum, modified starch and carageenan, and mixtures thereof. In some embodiments, the reductant component of a shave cream composition may advantageously include up to about 1% of a water-soluble thickener, such as hydroxyethyl cellulose.

As a thickener and/or for increased lubricity, the shave cream composition can also include a lubricious water-soluble polymer. Such polymers typically have a molecular weight of between about 300,000 daltons and about 15,000,000 daltons. Suitable polymers include, for example, polyvinylpyrrolidone (PVP), PVP/vinyl acetate copolymer, polyethylene oxide, polyacrylamide, and mixtures thereof. If a lubricious water-soluble polymer is included, it is typically provided in the shave cream composition in an amount of from about 0.005% to about 4%, preferably from about 0.01% to about 1.5%, of the composition. In some embodiments, a reductant component of a shave cream composition may advantageously include up to about 1% of a lubricious water-soluble polymer, such as polyacrylamide.

As discussed above, the heating reagents generally include an oxidizing agent, included in the oxidant component, and a reducing agent, included in the reductant component. Suitable oxidizing agents include peroxides, such as hydrogen peroxide (typically added as a 35% solution), benzoylperoxide, peroxomonosulfate, peroxodisulfate, urea hydrogen peroxide, and t-butyl peroxide. In some embodiments, the oxidant component of a shave cream composition may include from about 2% to about 10% of an oxidizing agent. In certain embodiments, the oxidant component can include from about 12% to about 16% of an oxidizing agent, such as hydrogen peroxide (35%) (which corresponds to about 4% to about 6% $H_2O_2$ active).

Suitable reducing agents are those that will react with the oxidizing agent when the two components of the formulation are mixed, to generate a perceptible exothermic reaction. Suitable reducing agents should also be safe for use on human skin in the amounts used in the formulation. The reducing agent may include, for example, thiosulfate and sulfite compounds, such as sodium sulfite, sodium thiosulfate (e.g., sodium thiosulfate pentahydrate), ammonium thiosulfate, potassium thiosulfate, and thiourea. Other suitable reducing agents include compounds with a thiourea backbone, such as 1,5-diethyl-2-thiobarbituric acid or its derivatives, or ascorbic acid. Mixtures of the above reducing agents, and other suitable reducing agents, may also be used. In some embodiments, the reductant component of a shave cream composition may include from about 2% to about 10%, preferably from about 3% to about 8%, of a reducing agent.

The oxidizing agent and reducing agent are generally included in approximately stoichiometric proportions, based on the redox reaction that will occur. The predominant redox reaction of hydrogen peroxide with sodium thiosulfate is as follows:

$$2S_2O_3^{2-}+H_2O_2 \rightarrow S_4O_6^{2-}+2OH^-$$

In the presence of an adequate amount of an effective catalyst, the reaction is as follows:

$$Na_2S_2O_3+4H_2O_2 \rightarrow Na_2SO_4+3H_2O+H_2SO_4$$

The total amount of the two agents is selected to provide a desired level of heat and duration of the exothermic reaction. Preferably, the maximum temperature obtained by the shave cream during the reaction is from about 30° C. to about 60° C., and this temperature is reached from about 10 seconds to about 45 seconds after the two components are mixed (this is the temperature the shave cream reaches when the oxidant component and the reductant component of the shave cream are mixed in a beaker in stoichiometric amounts that provide a total weight of 10 grams of the shave cream; when a typical amount of from about 5 grams to about 8 grams of shave cream is applied to the skin, the actual temperature on the skin is typically from about 28° C. to about 45° C.). When the oxidizing agents and reducing agents described above are used, the shave cream composition generally includes from about 2% to about 10% of the oxidizing agent and from about 2% to about 10% of the reducing agent, in approximately stoichiometric proportions.

To obtain the heat profile described above, it may be advantageous to include a catalyst in the shave cream composition. The catalyst is selected to catalyze the exothermic reaction, without deleterious effects on the skin or on the properties of the shave cream. The catalyst is generally included in the reductant component of the shave cream composition. Suitable catalysts for the exothermic reaction described above include sodium molybdate (e.g., sodium molybdate dihydrate), potassium molybdate, ammonium molybdate, sodium tungstate, potassium tungstate, and mixtures thereof. The composition generally includes 0.1% to about 1.5%, preferably about 0.2% to about 1.0%, of the catalyst.

If the exothermic reaction generates an acid, as the reaction of the oxidizing and reducing agents discussed above will generally do, it is preferred that the composition (e.g., the reductant component) also include a neutralizing agent (a neutralizer). The neutralizing agent is selected and provided in a sufficient amount to neutralize enough of the acid so that the exothermic reaction is complete and the shave cream composition will not irritate the user's skin. Preferably, substantially all of the acid is neutralized. Suitable neutralizing agents include, for example, triethanolamine, oxides (e.g., metal oxides), hydroxides (e.g., metal hydroxides), and metal carbonates, such as carbonates of alkaline metals (e.g., sodium, potassium), alkaline-earth metals (e.g., magnesium, barium), or transition metals (e.g., zinc). For example, the neutralizing agent may include calcium oxide, potassium hydroxide, sodium hydroxide, potassium bicarbonate, sodium bicarbonate or aluminum hydroxycarbonate. In some embodiments, the shave cream composition (preferably the reductant component of the shave cream composition) can include from about 0.5% to about 10% of such a neutralizer. For example, the reductant component can include about 1% calcium oxide or about 7% triethanolamine.

The shave cream composition can include additional non-ionic co-surfactants, typically in an amount of from about 1% to about 6%, preferably from about 2% to about 5%. The shave cream composition can also include additional amphoteric co-surfactants, typically in an amount of about 0.1% to about 3.0%, preferably from about 0.2% to about 1.5%. These additional surfactants are typically included in the reductant component unless they are also determined to be stable in the presence of oxidizing agent.

Suitable non-ionic co-surfactants include the fatty esters of polyhydro alcohols (e.g. polyglyceryl oleates), polyethylene oxide fatty esters of glycerides and fatty amides, particularly the alkyl-substituted fatty amides. These surfactants will generally have from about 6 to about 100, preferably from about 20 to about 50, ethylene oxide units per molecule. Typical non-ionic co-surfactants include, for example, PEG-40 hydrogenated castor oil and decaglycerol monooleate. Suitable amphoteric surfactants include, for example, the betaines and sultaines such as cocoamidopropyl betaine, coco dimethyl carboxymethyl betaine, coco sultaine and the like. These amphoteric surfactants may tend to function as cream boosters and stabilizers, providing additional heat stability for the cream and preventing puddling. It is preferred that the composition include from about 0.2% to about 1.5% of an amphoteric surfactant as a cream booster. Other suitable co-surfactants that can function as cream boosters include sodium lauroyl lactylate, sodium caproyl lactylate, and short-chain alkyl polyglucosides (e.g., alkyl polyglucosides with carbon chain lengths of C12 or less, such as lauryl glucoside, capryl glucoside, or caprylyl glucoside).

Although not necessary to forming a useful shave cream composition, other cosmetic ingredients may be advantageously added to improve the application aesthetics and/or achieve other shave benefits. Of course, such ingredients must be compatible and stable with either the reducing component or the oxidizing component. For example, the composition may include one or more of the following components: beard wetting agents, skin conditioning (e.g., exfoliating, moisturizing) agents (e.g., vitamin precursors and derivatives such as, for example, vitamins A, C and E, aloe, allantoin, panthenol, alpha-hydroxy acids, beta-hydroxy acids, phospholipids, triglycerides, botanical oils, amino acids), cream boosters (other than the cream-boosting co-surfactants described above), emollients (e.g., sunflower oil, fatty esters, squalane, quaternary compounds (e.g., polyquatemium-10), humectants (e.g., glycerin, sorbitol, pentylene glycol), phosphorus lipids (used, e.g., to encapsulate skin conditioning agents), fragrances, colorants, antioxidants, preservatives, and other such ingredients. In some embodiments, the reductant component of a shave cream composition can include from about 0.1% to about 1.5% of a fragrance.

The oxidant component and the reductant component are maintained separate from each other until the product is dispensed. This may be accomplished using any desired type of two-component packaging. The two components are mixed, either automatically upon dispensing from the package or manually by the user after dispensing, to form a uniform shave cream that becomes warm as the oxidizing and reducing agents react and that forms a lather upon spreading on the skin.

As will be illustrated below, the oxidant and reductant components may be formed by adding the oxidizing agent and reducing agent, respectively, to first and second shave cream bases. Preferably, the first and second shave cream bases are substantially identical. Thus, advantageously the oxidizing agent and the reducing agent, respectively, may be added to separate portions of the same shave cream base. The use of a single shave cream base to manufacture both components generally simplifies manufacturing, and may make the two components easier to mix during or after dispensing.

The shave creams described above may be formed using any suitable manufacturing process. An example of a suitable process is as follows.

Reductant component: An oil phase, containing non-ionic emulsifiers, fatty alcohols and thickeners, is blended at 75° C. The oil phase is added to a water phase at fast agitation and mixed at 75-80° C. for 30 minutes. A neutralizer is added under moderate agitation at 70° C. A reducing agent is added at 60° C. and a catalyst is added at 55° C. Upon further cooling and under continuous agitation, fragrance and dye are added at 40° C. Finally, the mixture is homogenized, using an external (IKA-type) homogenizer, to the consistency of a smooth cream.

Oxidant component: An oil phase, containing non-ionic emulsifiers, fatty alcohols and thickeners, is blended at 75° C. The oil phase is added to a water phase at fast agitation and mixed at 80° C. for 30 minutes. The mixture is cooled and subjected to moderate agitation using regular type propeller and side-scraper. The mixture is homogenized at 55° C. by passing through an external homogenizer to another mixing vessel. Oxidant is then added at 35° C. and mixed in well. Finally, the mixture is homogenized again to the consistency of a smooth cream.

The following examples are intended to be illustrative and non-limiting.

Example 1

A shave cream composition is prepared with the following components.

| Ingredients | REDUCTANT COMPONENT % by weight | OXIDANT COMPONENT % by weight |
|---|---|---|
| Water | 74.10 | 79.5 |
| Cetearyl Alcohol | 2.0 | 2.0 |
| Steareth-2 | 3.0 | 3.5 |
| Steareth-21 | 2.0 | 1.5 |
| Sodium molybdate | 0.7 | |
| Sodium thiosulfate pentahydrate | 6.5 | |
| Hydrogen peroxide (35%) | | 11.5 |
| Castor Wax | | 2.0 |
| Petrolatum | 3.0 | |
| Triethanolamine | 7.0 | |
| Fragrance | 1.0 | |
| FD&C Blue #1, 1% | 0.4 | |

Example 2

A shave cream composition is prepared with the following components.

| Ingredients | REDUCTANT COMPONENT % by weight | OXIDANT COMPONENT % by weight |
|---|---|---|
| Water | 71.3 | 78.0 |
| Cetyl Alcohol | 6.0 | 4.0 |
| Steareth-100 | 3.0 | |
| Steareth-21 | 2.0 | 4.0 |
| Sodium molybdate | 0.7 | |
| Sodium thiosulfate pentahydrate | 7.0 | |
| Hydrogen peroxide (35%) | | 14.0 |
| Polyacrylamide | 0.2 | |
| Polyquaternium-10 | 0.8 | |
| Triethanolamine | 7.0 | |
| Petrolatum | 1.0 | |
| PEG-150 Distearate | 0.3 | |
| Fragrance/Dye | 0.7 | |

When dispensed and mixed, the formulations described above create a dense warm cream on the skin, comparable to the type of cream that is generally observed when using soap-based shave creams, but without the negative attributes of soap-based creams. Application to the skin of an amount of shave cream suitable for use in shaving (approximately 8 grams) provides a pleasant warming sensation. The cream does not collapse with the heat and lasts for the entire period of shaving.

Other embodiments are within the scope of the following claims.

What is claimed is:

1. A self-heating non-aerosol shave cream product comprising:
    a container having a first chamber and a second chamber and at least one opening for dispensing the contents of said chambers;
    an oxidant component in the first chamber comprising a first shave cream base and an oxidizing agent, the first shave cream base being an oil-in-water emulsion comprising from about 55% to about 95% by weight of composition of a water continuous phase; and
    a reductant component in the second chamber comprising a second shave cream base and a reducing agent, the second shave cream base being an oil-in-water emulsion comprising from about 55% to about 95% by weight of composition of a water continuous phase;
    wherein each shave cream base is substantially free of soap and ionic surfactant,
    wherein at least one of said first shave cream base and said second shave cream bases comprises a non-ionic surfactant comprising one or more non-ethoxylated surfactant,
    wherein at least one of said first and second shave cream bases comprises an emollient, and
    wherein neither of the first shave cream base and the second shave cream base contains a volatile foaming agent.

2. The shave cream product of claim 1, wherein the oxidant component and the reductant component each independently comprises about 2% to about 15%, by weight of composition non-ionic surfactant.

3. The shave cream product of claim 1, wherein the oxidant component and the reductant component each independently comprises about 60% to about 90% by weight of composition water and about 3% to about 12% by weight of composition non-ionic surfactant.

4. The shave cream product of claim 2, wherein the non-ionic surfactant further comprises a fatty alcohol ethoxylate.

5. The shave cream product of claim 4, wherein the fatty alcohol ethoxylate comprises a C12-C24 hydrocarbon chain and a polyethylene oxide chain length of 2 to 150.

6. The shave cream product of claim 4, wherein the non-ionic surfactant comprises a blend of fatty alcohol ethoxylates comprising a fatty alcohol ethoxylate having from 2 to 20 ethoxy groups and a fatty alcohol ethoxylate having from 21 to 100 ethoxy groups.

7. The shave cream product of claim 5, wherein the first shave cream base and the second shave cream base each comprise less than about one percent of soap and ionic surfactant.

8. The shave cream product of claim 5, wherein the oxidant component comprises from about 2% to about 10% by weight of composition of the oxidizing agent and the reductant component comprises from about 2% to about 10% la weight of composition of the reducing agent.

9. The shave cream product of claim 5, wherein the first shave cream base and the second shave cream base each independently comprises a fatty alcohol.

10. The shave cream product of claim 1, wherein the first shave cream base and the second shave cream base each independently comprises about 2% to about 8% by weight of composition of a fatty alcohol.

11. The shave cream product of claim 1, wherein at least one of the first shave cream base and the second shave cream base comprises at least one member selected from the group consisting of a thickener and a fatty alcohol.

12. The shave cream product of claim 1 or 5, wherein the first shave cream base and the second shave cream base are substantially identical.

13. The shave cream product of claim 1, wherein the oxidizing agent comprises a peroxide.

14. The shave cream product of claim 1 or 13, wherein the reducing agent is selected from the group consisting of thiosulfate and sulfite compounds, thiourea compounds, and mixtures thereof.

15. The shave cream product of claim 1, wherein at least one of the first shave cream base and the second shave cream base comprises about 1% to about 15% by weight of composition of an emollient.

16. The shave cream product of claim 1 or 5, wherein at least one of the first shave cream base and the second shave cream base further comprises about 0.01% to about 10% by weight of composition of a thickener.

17. The shave cream product of claim 16, wherein the thickener comprises a water-insoluble thickener selected from ethoxylated fatty esters, fatty esters and high melting point waxes.

18. The shave cream product of claim 16, wherein the thickener comprises a water-insoluble thickener selected from PEG-150 distearate, PEG-150 pentaerythrityl tetrastearate, pentaerythrityl tetraisostearate, pentaerythrityl tetrastearate, isostearyl neopentanoate, and hydrogenated castor oil.

19. The shave cream product of claim 11, wherein the thickener comprises a blend of a water-soluble thickener and a water-insoluble thickener.

20. The shave cream product of claim 1, wherein the reductant component further comprises a catalyst selected to catalyze the exothermic reaction between the oxidizing agent and the reducing agent during use.

21. The shave cream product of claim 1, wherein at least one of the first shave cream base and the second shave cream base further comprises a neutralizing agent selected to neutralize acid generated by the exothermic reaction between the oxidizing agent and the reducing agent during use.

22. A self-heating non-aerosol shave cream product comprising:
a container having a first chamber and a second chamber;
an oxidant component in the first chamber comprising a first shave cream base and an oxidizing agent, the first shave cream base being an oil-in-water emulsion; and
a reductant component in the second chamber comprising a second shave cream base and a reducing agent, the second shave cream base being an oil-in-water emulsion;
wherein the oxidizing agent and the reducing agent are selected and being present in such proportion to provide a stoichiometric exothermic reaction upon mixing of the first shave cream base and the second shave cream base, wherein at least one of said first shave cream base and said second shave cream bases comprises a non-ionic surfactant comprising one or more non-ethoxylated surfactant, wherein at least one of said first and second shave cream bases comprises an emollient, wherein neither of the first shave cream base and the second shave cream base contains a volatile foaming agent, and wherein one of the first shave cream base and the second shave cream base comprises a colorant.

23. A self-heating non-aerosol shave cream product comprising:
a container having a first chamber and a second chamber;
an oxidant component in the first chamber comprising a first shave cream base being an oil-in-water emulsion and an oxidizing agent; and
a reductant component in the second chamber comprising a second shave cream base being an oil-in-water emulsion and a reducing agent;
wherein the oxidizing agent and the reducing agent are selected and being present in such proportion to provide a stoichiometric exothermic reaction upon mixing of the first shave cream base and the second shave cream base, wherein at least one of said first shave cream base and said second shave cream bases comprises a non-ionic surfactant comprising one or more non-ethoxylated surfactant, wherein at least one of said first and second shave cream bases comprises an emollient, wherein neither of the first shave cream base and the second shave cream base contains a volatile foaming agent, and wherein the first shave cream base has at least three ingredients that are identical to those in the second shave cream base.

24. The shave cream product of claim 23, wherein the at least three ingredients comprise water, a non-ionic surfactant, and a thickener.

25. The shave cream product of claim 23, wherein the first shave cream base has at least four ingredients that are identical to those in the second shave cream base.

26. The shave cream product of claim 25, wherein the at least four ingredients comprise water, a non-ionic surfactant, a thickener, and an fatty alcohol.

27. A self-heating non-aerosol shave cream product comprising:
a container having a first chamber and a second chamber and at least one opening for dispensing the contents of said chambers;
an oxidant component in the first chamber comprising a first shave cream base and an oxidizing agent, the first shave cream base being an oil-in-water emulsion; and
a reductant component in the second chamber comprising a second shave cream base and a reducing agent, the second shave cream base being an oil-in-water emulsion;
wherein at least one of said first shave cream base and said second shave cream bases comprises a non-ionic surfactant comprising one or more non-ethoxylated surfactant, wherein at least one of said first and second shave cream bases comprises an emollient, wherein neither of the first shave cream base and the second shave cream base contains a volatile foaming agent.

28. The shave cream product of claim 1, wherein said one or more non-ethoxylated surfactants is selected from the group consisting of polyglyceryl fatty esters, sugar ethers, sugar esters, esters of sugar derivatives.

29. The shave cream product of claim 1, wherein said first shave cream base, and said second shave cream base, each comprises an emollient.

30. The shave cream of claim 1, wherein said emollient is selected from the group consisting of mineral oil, petrolatum, squalane, squalene, hydrogenated polyisobutene, unsaturated polyisobutene, and mixtures thereof.

* * * * *